US010617612B2

(12) United States Patent
Park (10) Patent No.: US 10,617,612 B2
(45) Date of Patent: Apr. 14, 2020

(54) COMPOSITION COMPRISING DECANAL OR AS ACTIVE INGREDIENTS FOR PREVENTING HAIR LOSS OR STIMULATING HAIR GROWTH

(71) Applicant: INDUSTRY-ACADEMIC COOPERATION FOUNDATION, YONSEI UNIVERSITY, Seodaemun-gu (KR)

(72) Inventor: Tae Sun Park, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 15/782,567

(22) Filed: Oct. 12, 2017

(65) Prior Publication Data

US 2018/0104162 A1  Apr. 19, 2018

(30) Foreign Application Priority Data

Oct. 13, 2016  (KR) .................. 10-2016-0132827

(51) Int. Cl.
| | |
|---|---|
| *A61K 8/33* | (2006.01) |
| *A23L 33/10* | (2016.01) |
| *A23L 33/00* | (2016.01) |
| *A23L 2/52* | (2006.01) |
| *A61Q 7/00* | (2006.01) |
| *A61P 17/00* | (2006.01) |
| *A61P 17/14* | (2006.01) |

(52) U.S. Cl.
CPC .................. *A61K 8/33* (2013.01); *A23L 2/52* (2013.01); *A23L 33/10* (2016.08); *A23L 33/30* (2016.08); *A61Q 7/00* (2013.01); *A23V 2002/00* (2013.01); *A61K 2800/92* (2013.01); *A61P 17/00* (2018.01); *A61P 17/14* (2018.01)

(58) Field of Classification Search
CPC . A23L 2/52; A23L 33/10; A23L 33/30; A23V 2002/00; A61K 2800/92; A61K 8/33; A61Q 7/00; A61P 17/00; A61P 17/14
See application file for complete search history.

(56) References Cited

U.S. PATENT DOCUMENTS 5,322,689 A * 6/1994 Hughes ................ A61K 8/8147
424/401
9,364,409 B2 * 6/2016 Li ............................ A61K 8/33
9,636,289 B2 * 5/2017 Park ................... A61K 31/7048

FOREIGN PATENT DOCUMENTS

KR  10-2015-0085970   7/2015
WO  WO-2017182821 A1 * 10/2017 ............... A61K 8/33

OTHER PUBLICATIONS

Jo et al., "Valproic acid promotes human hair growth in in vitro culture model", 2013, Journal of Dermatological Science, 72(1), pp. 16-24. (Year: 2013).*
Suo et al., "Dietary vitamin A regulates wingless-related MMTV integration site signaling to alter the hair cycle", 2015, Experimental Biology and Medicine, 240(5), pp. 618-623. (Year: 2015).*
National Center for Biotechnology Information. PubChem Database. Decanal, CID=8175, https://pubchem.ncbi.nlm.nih.gov/compound/8175 (Create: Sep. 16, 2004; Accessed on Mar. 29, 2019; 58 pages total). (Year: 2004).*
National Institutes of Health. National Institute of Arthritis and Musculoskeletal and Skin Diseases. Cicatricial Alopecia. https://www.niams.nih.gov/health-topics/cicatricial-alopecia (Last Reviewed: Dec. 30, 2012; Accessed on Mar. 29, 2019; 4 pages total). (Year: 2012).*
National Institutes of Health. National Institute of Arthritis and Musculoskeletal and Skin Diseases. Alopecia Areata. https://www.niams.nih.gov/health-topics/alopecia-areata (Last Reviewed: May 31, 2016; Accessed on Mar. 29, 2019; 5 pages total). (Year: 2016).*
Harvard Health Publishing. Harvard Medical School. Alopecia Areata. https://www.health.harvard.edu/a_to_z/alopecia-areata-a-to-z Published: Jan. 2019. (3 pages total). (Year: 2019).*
National Institutes of Health. Lister Hill National Center for Biomedical Communications. U.S. National Library of Medicine. https://ghr.nlm.nih.gov/condition/androgenetic-alopecia (Reviewed: Aug. 2015; Published: Mar. 19, 2019) (Year: 2019).*
Kurita et al., "Antifungal Activity of Components of Essential Oils", 1981, Agricultural and Biological Chemistry, 45:4, pp. 945-952 (DOI: 10.1080/00021369.1981.10864635) (Year: 1981).*

* cited by examiner

*Primary Examiner* — My-Chau T. Tran
(74) *Attorney, Agent, or Firm* — Norton Rose Fulbright US LLP (57) ABSTRACT

A composition for preventing hair loss or promoting hair growth comprising Decanal or pharmaceutically acceptable salt thereof as an active ingredient is provided. In particular, the composition relates to a quasi-drug, a cosmetic composition, a health functional food composition, and a pharmaceutical composition for preventing hair loss or promoting hair growth, which exhibits an excellent and stable effect on hair growth and hair growth, even while comprising a natural compound which has no side effect even in long-term administration in a chronic disease as an active ingredient.

6 Claims, 6 Drawing Sheets
Specification includes a Sequence Listing.

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
ttttggccac tcctcttcct                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2 tcctttcca accgaaaacc                                                20

<210> SEQ ID NO 3
<211> LENGTH: 24
<212> TYPE: DNA
<213> ORGANISM: Artificial Sequence
<220> FEATURE:
<223> OTHER INFORMATION: Synthetic Primer

<400> SEQUENCE: 3
ttctatgaac aggcctttcg ttct                                          24

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
cctcgtgtag aacttcctcc                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
aagggtccac aaggtcaagg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
agaagcacag atggctgcac                                               20

<210> SEQ ID NO 7
<211> LENGTH: 20
<212> TYPE: DNA
<213> ORGANISM: Artificial Sequence

```
<220> FEATURE:
<223> OTHER INFORMATION: Synthetic Primer

<400> SEQUENCE: 7
tgtgtgagga acagaactca                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
cctacagccc tagtcatcag                                               20

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
tgcagagtcc caaaatgaat g                                             21

<210> SEQ ID NO 10
<211> LENGTH: 18
<212> TYPE: DNA
<213> ORGANISM: Artificial Sequence
<220> FEATURE:
<223> OTHER INFORMATION: Synthetic Primer

<400> SEQUENCE: 10
gagcctgtcc ttgtgtac                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetic Primer

<400> SEQUENCE: 11
atggctactc aagctgac                                                 18

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
cagcactttc agcactctgc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
tcaacaagcc cacagggtat                                               20
```

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
actcgtgcag agcaaaggat                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
cgaggccatg gtgctatact                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
acaccagggt gattgagacc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
tcttcaagcc atcctgtgtg                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
gcgagtctgt gttttttgcag                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
gacatggatc ctgccaactt                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

```
<400> SEQUENCE: 20
aattccaact gccactgtcc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
agaacatcat ccctgcatcc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
tccaccaccc tgttgctgta                                              20
```

COMPOSITION COMPRISING DECANAL OR AS ACTIVE INGREDIENTS FOR PREVENTING HAIR LOSS OR STIMULATING HAIR GROWTH

CROSS-REFERENCE TO RELATED APPLICATION

This application claims priority to and the benefit of Korean Patent Application No. 10-2016-0132827, filed on Oct. 13, 2016. The contents of the referenced application are incorporated into the present application by reference.

1. FIELD OF THE DISCLOSURE

The present disclosure relates to a composition for preventing hair loss or promoting hair growth comprising Decanal or pharmaceutically acceptable salt thereof as an active ingredient.

2. DISCUSSION OF RELATED ART

According to the National Health Insurance Corporation's Health Insurance Policy Institute's analysis of health insurance payment data from 2001 to 2008, the number of actual patients treated with 'hair loss disease' was 103,000 in 2001, 142,000 in 2005, and 165,000 in 2008, increased by 60% over the last seven years. By age, the number of patients in the 20s and 40s was 114,000, accounting for 69.5% of the patients, and the number of patients under 10 was more than 22,000. By sex, as of 2008, the number of patients actually treated was 84,000 for males and 80,000 for females, with males slightly more than females, As of 2008, the number of patients treated with 'hair loss' disease by domestic disease in domestic health insurance department was in the order of alopecia areata (130,000 people), scarred alopecia (20,000 people), androgenic alopecia (9,000), and other non-scarring hair loss (8,000).

Meanwhile, according to the June 2003 International Hair and Cosmetic Research Debate, worldwide, 250 million people are suffering from hair loss, and the incidence of hair loss was around 30 to 65% at 24 to 50 years old. As of 2008, China's hair loss population is about 300 million people, 30% of men population in their 30s and 50% of men population in their 50s have hair loss symptoms, the number of patients with hair loss is increasing by 10 to 15% every year. According to a survey of company that sells wigs and performs hair transplant surgery for Japanese in 2007, the rate of Japanese hair loss was 26.5%, the estimated population of patients with hair loss was estimated at 12.93 million.

Currently, treatments for hair loss treatment are classified into pharmaceuticals, quasi-drugs, and cosmetics. The prescription medicine that can be purchased with a doctor's prescription is "propecia" which is developed and sold by Merck in the United States. Finasteride which is a major component of propecia received approval for hair loss treatment from the US FDA in December 1997. The finasteride is an inhibitor of 5-α-reductase enzyme that converts testosterone to dihydrotestosterone (DHT), and acts to grow thin hair into thick and long hair. The finasteride is effective in improving hair loss in the short term, but it has side effects such as erectile dysfunction, sexual dysfunction, and male breast enlargement. Minoxidil is a safe and effective medicine that can be purchased without a doctor's prescription, and it was approved by the US FDA as the first hair loss treatment in December 1997. This drug has the effect of promoting hair growth by improving blood circulation and opening the potassium channel, but local reactions such as itching, rashes and the like, and tachycardia may occur.

As a product approved by Ministry of Food and Drug Safety (KFDA) for hair loss prevention and hair growth function, There are products such as 'Hair Force Competent' of CJ Lion, 'Hair Tonic' of Moracle and 'Mo&Moa' of LG household & health care, which are typical quasi-drugs that can be sold at supermarkets and convenience stores by the Minister of Health and Welfare. As cosmetics, shampoo or products used for scalp or hair to maintain or promote skin and hair health are being sold.

Human hair loss cycle is largely divided into anagen, catagen, and telogen. Anagen is a period when the activity of the papillae is active and cell division is vigorous and the hair grows at a rapid rate. The life span of the anagen varies depending on the type of hair, but in the case of hair, it is about 3 to 6 years. Anagen hair accounts for 80-90% of the total hair, and people who are undergoing hair loss have a hair cycle which of short anagen and long telogen, and the proportion of the anagen hair in the whole hair are decreased. Catagen is a period when the anagen of the hair ends and the hair production is getting slower and eventually stops cell division and growth. It lasts for 1 to 1.5 months, and about 1% of total hair is in this stage. Telogen is a last stage of growth, in which the hair follicles and papilla are completely separated and the hair follicles are atrophied, the hair roots go up further and the hair is removed. Telogen lasts 3 to 4 months and 4 to 14% of total hairs are in this stage. When telogen ends and the activity of the papilla are activated again, the new hair's papilla is made, and the hair on the telogen is pushed out and completely out of the scalp.

Decanal is an aldehydes-based compound, also named aldehyde C-10, caprinaldehyde, decyl aldehyde, decanaldehyde, and the like, the structure is $C_{10}H_{20}O$ and the molecular weight is 156.2 g/mol.

SUMMARY OF THE DISCLOSURE

Accordingly, the present inventors sought to discover naturally occurring compounds that can prevent hair loss or promote hair growth without side effects. As a result, the mechanism of altering the expression of hair growth promoting proteins and genes of Decanal was identified.

An object of the present disclosure is made to solve the above problems, and thus is to provide a pharmaceutical composition for preventing hair loss or promoting hair growth comprising Decanal or pharmaceutically acceptable salt thereof as an active ingredient.

Another object of the present disclosure is to provide a quasi-drug for preventing hair loss or promoting hair growth comprising Decanal or pharmaceutically acceptable salt thereof as an active ingredient.

Another object of the present disclosure is to provide a cosmetic composition for preventing hair loss or promoting hair growth comprising Decanal or pharmaceutically acceptable salt thereof as an active ingredient.

Another object of the present disclosure is to provide a health functional food composition for preventing hair loss or promoting hair growth comprising Decanal or pharmaceutically acceptable salt thereof as an active ingredient.

Another object of the present disclosure is to provide a method for preventing hair loss or promoting hair growth comprising administering a composition containing Decanal or pharmaceutically acceptable salt thereof as an active ingredient.

However, the technical problem to be solved by the present disclosure is not limited to the above-mentioned problems, and other matters not mentioned can be clearly understood by a person skilled in the art from the following description.

Therefore, the present disclosure provides a pharmaceutical composition for preventing hair loss or promoting hair growth which comprises Decanal or pharmaceutically acceptable salt thereof as an active ingredient.

In an exemplary embodiment of the present disclosure, the composition may increase an expression of a protein selected from a group consisting of Wigless related MMTV integration site 10b (Wnt10b), Frizzled receptor 1 (FZD1), Low-density lipoprotein receptor-related protein 5 (LRP5), Insulin-like growth factor 1 (IGF1), β-catenin, vascular endothelial growth factor (VEGF), hepatocyte growth factor (HGF) and keratocyte growth factor (KGF).

In another exemplary embodiment of the present disclosure, the composition may decrease an expression of glycogen synthase kinase 3β (GSK3β) or Axin.

In another exemplary embodiment of the present disclosure, the composition may be a formulation selected from a group consisting of a cream, a gel, a patch, a spray agent, an ointment agent, a plaster agent, a lotion agent, a liniment agent, a pasta agent or a cataplasma agent as a skin external preparation.

In addition, the present disclosure provides a cosmetic composition for preventing hair loss or promoting hair growth which comprises Decanal or pharmaceutically acceptable salt thereof as an active ingredient.

In an exemplary embodiment of the present disclosure, the cosmetic composition may be a formulation of a hair tonic, a hair lotion, a hair cream, a hair spray, a hair mousse, a hair gel, a hair conditioner, a hair shampoo, a hair rinse, a hair pack, a hair treatment, an eyebrow hair growth treatment, an eyelash hair growth treatment, an eyelash nutrient, a pet shampoo or a pet rinse.

In addition, the present disclosure provides a health functional food composition for preventing hair loss or promoting hair growth which comprises Decanal or pharmaceutically acceptable salt thereof as an active ingredient.

According to the present disclosure to solve the above problems, there may be provided a composition for preventing hair loss or promoting hair growth which comprises Decanal or pharmaceutically acceptable salt thereof as an active ingredient.

The composition of the present disclosure may be usefully used as a quasi-drug, a cosmetic composition, a health functional food composition, and a pharmaceutical composition for preventing hair loss or promoting hair growth, which exhibits an excellent and stable effect on hair growth and hair growth, even while comprising a natural compound which has no side effect even in long-term administration in a chronic disease as an active ingredient.

BRIEF DESCRIPTION OF THE DRAWINGS

FIG. 3A-C illustrates the result of histological observation of back skin of the mice to which each sample was applied for 4 weeks.

DETAILED DESCRIPTION OF EXEMPLARY EMBODIMENTS

Hereinafter, the present disclosure will be described in more detail.

As described above, as hair loss due to stress in addition to hormone secretion changes increases, although the demand for a pharmaceutical composition capable of preventing hair loss (or alopecia) and promoting hair growth has been increased, among the compounds known to be safe for human body, few compounds have been reported that are effective in preventing hair loss and/or promoting hair growth.

Decanal of the present disclosure can be used to regulate the expression of hair growth related genes and proteins in skin tissue, therefore since a hair growth promoting effect can be significantly exhibited in a hairless mouse, there is an effect of providing a composition effective in preventing hair loss and promoting hair growth.

Accordingly, the present disclosure provides a pharmaceutical composition for preventing hair loss or promoting hair growth comprising Decanal or pharmaceutically acceptable salt thereof as an active ingredient.

The term "Decanal" of the present disclosure is an aldehyde-based compound represented by the following general Formula 1, which is widely used as a fragrance ingredient and flavoring agent.

Formula 1

It was reported that Decanal was applied to embryos of sea urchins and copepods (aquatic animals such as *daphnia magna* and the like) as a physiological activity of conventional Decanal, as a result, a reproductive failure was induced by inducing apoptosis, and Decanal and N-amino-N'-1-octylguanidine (AOG) were mixed to treat tumor cells which were HeLa cells and bacteria, as a result, synergistic activity and hinders growth. It was also reported that strong nematicidal activity of decanal prevents and inhibits nematode parasitic on plant roots. However, in the present disclosure, by revealing the mechanism of regulation of the expression of hair-related genes and proteins in Decanal, a new use of Decanal for preventing hair loss or promoting hair growth is identified.

The term "hair loss" of the present disclosure means a phenomenon in which hair completely escapes from the scalp. People who are undergoing hair loss have a hair cycle which of short anagen and long telogen, as demonstrated in the following examples, it was confirmed that Decanal converts hair from telogen to anagen, and has an effect of preventing, ameliorating or treating hair loss by increasing an expression of hair growth and a growth factor related to hair growth in skin tissue.

The term "hair generation" of the present disclosure means that the hair grows from the scalp, "hair growth" means the length of hair is getting longer (for example, growth of hair) and is used interchangeably the term "hair nurturing" as another term used in the art.

The composition of the present disclosure may increase the expression of a protein selected from the group consisting of Wigless related MMTV integration site 10b (Wnt10b), Frizzled receptor 1 (FZD1), Low-density lipoprotein receptor-related protein 5 (LRP5), Insulin-like growth factor 1 (IGF1), β-catenin, vascular endothelial growth factor (VEGF), hepatocyte growth factor (HGF) and keratocyte growth factor (KGF). Specifically, as described in Example 2 of the present disclosure, it might be confirmed that the composition of the present disclosure not only increases the expression of IGF1, VEGF, HGF and KGF which were growth factors affecting hair generation and hair growth in skin tissue, but also significantly increases expression of Wnt10b, FZD1, LRP5 which were Wnt/β-catenin signal transduction material as compared to a negative control group. In addition, it might be confirmed that the expression amount of the protein or gene is significantly increased as compared to a group treated with Minoxidil which was a representative drug that can promote hair generation and hair growth.

In addition, a composition of the present disclosure may be one which decreases the expression of glycogen synthase kinase 3β (GSK3β) or Axin. Specifically, as described in Example 2 of the present disclosure, it was confirmed that the composition of the present disclosure increased the expression of Wnt10b, thereby decreasing the expression of GSK3β and Axin. Therefore, the composition of the present disclosure is more harmless to the human body than the conventional synthetic composition, and it can be usefully used as a hair growth or hair tonic composition exhibiting various and stable hair generation and hair growth promoting effects.

Decanal is preferably a skin external (or dermatological) composition, and thus the skin external pharmaceutical composition of the present disclosure comprising Decanal as an active ingredient can be prepared and used as a pharmaceutical composition in the form of an external preparation for skin such as a cream, a gel, a patch, a spray agent, an ointment agent, a plaster agent, a lotion agent, a liniment agent, a pasta agent or a cataplasma agent as a skin external preparation for preventing hair loss and improving hair growth and promoting, but is not limited thereto.

The compound of the present disclosure can be used in the form of a pharmaceutically acceptable salt, and as the salt, acid addition salt formed by pharmaceutically acceptable free acids are useful. The acid addition salt are obtained from inorganic acids such as hydrochloric acid, nitric acid, phosphoric acid, sulfuric acid, hydrobromic acid, hydroiodic acid, nitrous acid or phosphorous acid, and aliphatic mono- and dicarboxylates, and Phenyl-substituted alkanoates, hydroxyalkanoates and alkanedioates, and non-toxic organic acids such as aromatic acids, aliphatic and aromatic sulfonic acids.

Such pharmacologically non-toxic salt include a sulfate, a fatty sulphate, a bisulfate, a sulfite, a bisulfite, a nitrate, a phosphate, a monohydrogenphosphate, a dihydrogenphosphate, a metaphosphate, a pyrophosphate chloride, a bromide, an iodide, a fluoride, an acetate, a propionate, a decanoate, a caprylate, an acrylate, a formate, an isobutyrate, a caprate, a heptanoate, a propiolate, an oxalate, a malonate, a however, a surveyor, a sebakate, a fumarate, a maliite, a butyne-1,4-dioate, a hexane-1,6-dioate, a benzoate, a chlorobenzoate, a methyl benzoate, a dinitrobenzoate, a hydroxybenzoate, a methoxybenzoate, a phthalate, a terephthalate, a benzene sulfonate, a toluene sulfonate, a chlorobenzene sulfonate, a xylene sulfonate, a phenylacetate, a phenyl propionate, a phenyl butyrate, a citrate, a lactate, a β-hydroxybutyrate, a glycolate, a malate, a tartrate, a methane sulfonate, a propane sulfonate, a naphthalene-1-sulfonate, a naphthalene-2-sulfonate, or a mandele.

The acid addition salt according to the present disclosure can be prepared by conventional method, for example a method comprising: dissolving Decanal in an excess amount of an aqueous acid solution and precipitating the salt by using a water-miscible organic solvent, for example: such as methanol, ethanol, acetone or acetonitrile. The acid addition salt can be also prepared by heating an equivalent amount of Decanal and an acid or alcohol in water, and then evaporating and drying the mixture resulted or performing suction filtration of the precipitated salt.

In addition, bases can be used to make pharmaceutically acceptable metal salt.

The alkali metal or alkaline earth metal salt is obtained, for example, by dissolving the compound in an excess amount of an alkali metal hydroxide or alkaline earth metal hydroxide solution, filtering the insoluble compound salt, and evaporating and drying the filtrate. At this time, it is preferable from a pharmaceutical point of view to produce sodium, potassium or calcium salt, as a metal salt. In addition, the corresponding silver salt is obtained by reacting an alkali metal or alkaline earth metal salt with a suitable silver salt (for example, silver nitrate).

In addition, the Decanal of the present disclosure includes not only pharmaceutically acceptable salt, but also all salts, hydrates and solvates which can be prepared by conventional methods.

The addition salt according to the present disclosure can be prepared by a conventional method, and for example, can be prepared by dissolving Decanal in a water-miscible organic solvent, for example, acetone, methanol, ethanol, or acetonitrile, adding an excessive amount of an organic acid or an aqueous acid solution of an inorganic acid, and followed by precipitation or crystallization. Subsequently, an additional salt may be obtained by evaporating a solvent or an excess acid from the mixture and then dried, or be prepared by suction filtration of the precipitated salt.

When the composition of the present disclosure is used as a medicine, a pharmaceutical composition containing Decanal or a pharmaceutically acceptable salt thereof as an active ingredient may be formulated into various oral administration or parenteral administration forms at the time of clinical administration, but the present disclosure is not limited thereto.

Examples of formulations for oral administration include tablets, pills, hard/soft capsules, liquids, suspensions, emulsions, syrups, granules, and elixirs and the like, and these formulations may contain, in addition to the active ingredient, a diluent (for example, lactose, dextrose, sucrose, mannitol, sorbitol, cellulose and/or glycine), a lubricant (for example, silica, talc, stearic acid and its magnesium or calcium salt thereof and/or polyethylene glycol). Tablets may also contain binders such as magnesium aluminum silicate, starch paste, gelatin, methylcellulose, sodium carboxymethylcellulose and/or polyvinylpyrrolidine and may optionally contain disintegrating agents such as starch, agar, alginic acid or sodium salt thereof, or effervescent mixtures and/or absorbents, coloring agents, flavoring agents, and sweetening agents.

The pharmaceutical composition comprising decanal or a pharmaceutically acceptable salt thereof as an active ingredient of the present disclosure may be administered parenterally, and the parenteral administration may be by subcutaneous injection, intravenous injection, intramuscular injection or intrasternal injection.

At this time, to formulate the formulation for parenteral administration, the decanal or a pharmaceutically acceptable salt thereof may be mixed in water with a stabilizer or a buffer to prepare a solution or suspension, which is then manufactured in the form of an ampoule or vial unit administration. The composition may be sterilized and/or contain adjuvants such as preservatives, stabilizers, wettable or emulsifying accelerators, salt for controlling osmotic pressure and/or buffers and the like, and other therapeutically useful substances, and be formulated according to a conventional method of mixing, granulating or coating.

In addition, the dose of the compound of the present disclosure to the human body may vary depending on the age, weight, sex, dosage form, health condition and disease severity of the patient, and is generally 0.001-1,000 mg/day, preferably 0.01 to 500 mg/day, based on adult patients having a body weight of 60 kg, and it may be administered once or several times a day at intervals of a predetermined time depending on the judgment of a doctor or pharmacist.

In addition, the present disclosure provides a quasi-drug for preventing hair loss or promoting hair growth comprising Decanal or pharmaceutically acceptable salt thereof as an active ingredient. The specific contents of decanal are as described above.

When decanal of the present disclosure is used as an active ingredient of a quasi-drug composition, it is possible to add Decanal, which exhibits hair loss preventing and hair growth promoting effect, as it is, or Decanal can be used with other quasi-drugs or component of quasi-drugs, and can be appropriately used according to a conventional method. The amount of the active ingredient to be mixed can be appropriately determined depending on the purpose of use.

A quasi-drug composition for preventing hair loss and promoting hair growth of the present disclosure is not particularly limited in its formulation, and may be variously formulated in the form of quasi-drugs known in the art to exhibit hair loss preventing and hair growth promoting effects. The formulated quasi-drugs include a hair tonic, a hair lotion, a hair cream, a hair spray, a hair mousse, a hair gel, a hair conditioner, a hair shampoo, a hair rinse, a hair pack, a hair treatment, an eyebrow hair growth treatment, an eyelash hair growth treatment, an eyelash nutrient, a pet shampoo, a pet rinse, a hand cleaner, a detergent soap, a soap, a disinfectant cleaner, a wet tissue, a mask, an ointment, a patch or a filter filler and the like, and includes all quasi-drugs in the conventional sense.

In addition, the quasi-drug composition for preventing hair loss and for promoting hair growth in each formulation can be blended with other components arbitrarily selected depending on the formulation of the other quasi-drugs, or the purpose of use, and the like. The amount of the active ingredient to be mixed may be appropriately determined depending on the purpose of use, and the quasi-drug composition may include, for example, conventional additives such as thickeners, stabilizers, solubilizers, vitamins, pigments and perfumes, and carriers.

The content of the composition is preferably 0.0001 to 10% by weight based on the total weight, when it is more than 10% by weight, the color and stability of the composition are decreased, when it is less than 0.0001% by weight, the effect is insignificant. The quasi-drug composition comprising Decanal as an active ingredient of the present disclosure has little toxicity and side effects to cells as confirmed by the treatment index, and thus can be useful as a quasi-drug material.

In addition, the present disclosure provides a cosmetic composition for preventing hair loss or promoting hair growth comprising Decanal or pharmaceutically acceptable salt thereof as an active ingredient.

The components contained in the cosmetic composition of the present disclosure include components commonly used in cosmetic compositions in addition to decanal or pharmaceutically acceptable salt thereof as an active ingredient and include, for example, conventional adjuvants such as antioxidants, stabilizers, dissolving agents, vitamins, pigments and perfumes, and carriers.

The cosmetic composition of the present disclosure may be prepared in any formulation conventionally produced in the art and may be, for example, in the formulation of a solution, a suspension, an emulsion, a paste, a gel, a cream, a lotion, a powder, a soap, a surfactant-containing cleansing, oils, powder foundations, emulsion foundations, wax foundations and sprays, but is not limited thereto.

An animal oil, vegetable oil, wax, paraffin, starch, tracant, cellulose derivative, polyethylene glycol, silicone, bentonite, silica, talc or zinc oxide may be used as the carrier component, when the formulation of the present disclosure is a paste, a cream or a gel.

Lactose, talc, silica, aluminum hydroxide, calcium silicate or polyamide powder may be used as the carrier component, when the formulation of the present disclosure is a powder or a spray, and in particular, propellants such as chlorofluorohydrocarbons, propane/butane or dimethyl ether may be further included, when the formulation is the spray.

A solvent, a solubilizing agent or an emulsifying agent may be used as the carrier component, when the formulation of the present disclosure is the solution or the emulsion, and for example, the carrier component may include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or fatty acid esters of sorbitan.

Liquid diluents such as water, ethanol or propylene glycol, a suspension such as ethoxylated isostearyl alcohol, polyoxyethylene sorbitol ester and polyoxyethylene sorbitan ester, or microcrystalline cellulose, aluminum metahydroxide, bentonite, agar or tracant, or the like, may be used as the carrier component, when the formulation of the present disclosure is the suspension.

Aliphatic alcohol sulfates, aliphatic alcohol ether sulfate, sulfosuccinic acid monoester, isethionate, imidazolidine derivatives, methyl taurate, sarcosinate, fatty acid amide ether sulfate, alkylamido betaine, aliphatic alcohols, fatty acid glycerides, fatty acid diethanolamide, vegetable oils, lanolin derivatives or ethoxylated glycerol fatty acid esters, or the like, may be used as the carrier component, when the formulation of the present disclosure is a surfactant-containing cleansing.

In addition, the present disclosure provides a health functional food composition for preventing hair loss or promoting hair growth comprising Decanal or pharmaceutically acceptable salt thereof as an active ingredient.

The food composition according to the present disclosure can be prepared in various forms according to conventional methods known in the art. A general food may be prepared by adding the Decanal of the present disclosure to beverages (including alcoholic beverages), fruits and processed foods thereof (for example, canned fruits, bottled foods, jam, marmalade, and the like), fish, meat and processed foods thereof (for example, ham, sausage, confection, and the like), breads and noodles (for example, udon, buckwheat noodles, ramen, spaghetti, macaroni, and the like), fruit juice, various drinks, cookies, peas, dairy products (for example, butter, cheeses, and the like), edible vegetable oil, margarine, vegetable protein, retort food, frozen food, various seasonings (for example miso, soy sauce, sauces, and the like), or the like, but are not limited thereto. In addition, the nutritional adjuvant may be prepared by adding decanal of the present disclosure to capsules, tablets, pills and the like, but are not limited thereto. In addition, as the health functional foods, for example, Decanal itself of the present disclosure can be provided by liquefaction, granulation, encapsulation and pulverization so as to be drinkable (a health beverage) or ingested by preparing in the form of tea, juice, and drink, and the like, but are not limited thereto. In addition, Decanal of the present disclosure may be used in the form of a powder or a concentrate to use as a food additive. In addition, by mixing the Decanal of the present disclosure with known active ingredients known to be effective in hair loss preventing and hair growth promoting, it can be prepared in the form of a composition.

When Decanal of the present disclosure is used as the health beverage, the health beverage composition may contain various flavoring agents or natural carbohydrates as an additional ingredient like conventional beverages. The above-described natural carbohydrates may include monosaccharides such as glucose and fructose; disaccharides such as maltose, sucrose; polysaccharides such as dextrin, cyclodextrin; and sugar alcohols such as xylitol, sorbitol and erythritol. Sweeteners may include natural sweeteners such as tau Martin and stevia extract; and synthetic sweeteners such as saccharin and aspartame, and the like. The ratio of the natural carbohydrate is generally about 0.01 to 0.04 g, preferably about 0.02 to 0.03 g, per 100 mL of the composition of the present disclosure.

In addition, Decanal of the present disclosure can be contained as an active ingredient of a health functional food for preventing hair loss and promoting hair growth, and the amount of Decanal is not particularly limited to an amount effective for achieving hair loss preventing and hair growth promoting effect, but is preferably 0.01 to 100% by weight based on the total weight of the total composition. The food composition of the present disclosure can be prepared by mixing other active ingredients known to be effective for hair loss preventing and hair growth promoting effect together with Decanal.

In addition to the above, the health food of the present disclosure may contain various nutrients, vitamins, electrolytes, flavors, colorants, pectic acid, salts of pectic acid, alginic acid, salts of alginic acid, organic acids, protective colloid thickeners, pH adjusters, stabilizers, preservatives, glycerin, alcohols or carbonating agents, or the like. In addition, the health food of the present disclosure may contain fruit pulp for the production of natural fruit juice, fruit juice beverage, or vegetable beverage. These components may be used independently or in combination. The proportion of such additives is not critical, but is generally selected in the range of 0.01 to 0.1 parts by weight per 100 parts by weight of the composition of the present disclosure.

Hereinafter, the present disclosure will be described in detail with reference to examples. However, these examples are for further illustrating the present disclosure, and the scope of the present disclosure is not limited to these examples.

EXAMPLES

Example 1. Efficacy of Decanal to Promote Hair Growth 1-1. Breeding of Experimental Animals and Subcutaneous Injection of Hair Growth Treatment (1) Preparation of Sample Ethanol:water:propylene glycol=5:3:2 which used as vehicle, minoxidil (MXD) which was a reference drugs, and Decanal which was an experimental material, was all purchased from Sigma-Aldrich Co.

(2) Experimental Animal Breeding

Twenty-four 6-week-old male C57BL/6N mice were purchased from Orientbio Inc. and were adapted to the breeding environment for 2 weeks, the experimental groups were divided into three groups (n=5): negative control (CON), positive control (MXD) and Decanal (DC) groups, and were used for experiments. The animals were kept in a temperature of 21±2.0° C., relative humidity of 50±5%, and 12 hours of day and night cycles. During the experiment, the mice were fed with a regular solid feed (chow) with water freely.

(3) Skin Application and Visual Observation Method

To examine the effect of promoting hair growth, 8-week-old mouse of telogen hair showing pink color of dorsal skin was used. After removing the hair of the mouse backing using a clipper for a mouse, the sample was applied once a day at 4:00 PM for four weeks. Decanal (3 mg/mouse/day) which is experimental material and minoxidil (3 mg/mouse/day) used as a reference drug were dissolved in vehicle (ethanol:water:propylene glycol=5:3:2) and applied, and the vehicle only was applied to the negative control group.

To visually confirm the state of hair growth, after the animals were lightly anesthetized with ether, the back was photographed, at the end of one week, two weeks, three weeks, and four weeks after application begins, Hair length was measured using a ruler to evaluate the degree of hair growth.

1-2. Measurement of Body Weight Change

The body weight of the experimental animals was measured weekly from immediately before application of the hair growth treatment to the end of application. There was no significant difference in the initial body weights of the negative control group (CON group), the experimental group (DC group), and the positive control group (MXD group), and the body weights measured after 4 weeks of application of the experimental material were also not significantly different between the experimental groups.

Figure 1:
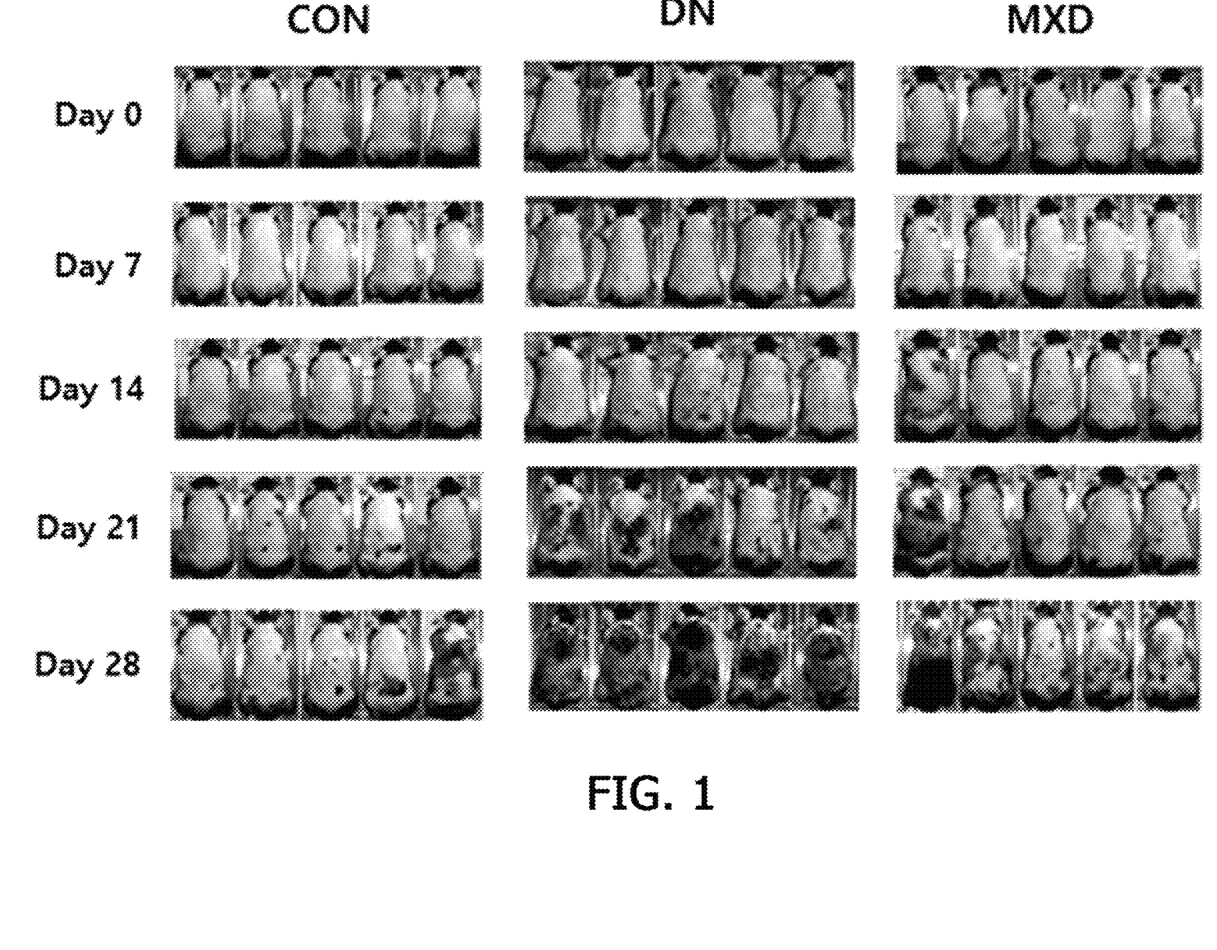
FIG. 1 is a photograph illustrating regrowth of hair with the elapsed days of administration of each sample in mice model which the hair is epilated.

1-3. Changes in Hair Growth Condition and Hair Length (1) Visual Features of Hair Growth The sample was applied to the back of the mice for 4 weeks, and the appearance of the hair growing each week was photographed and confirmed. The mouse that entered the telogen had a pinkish color on the body surface when the hair was epilated. When the body surface color turns black as the experiment progresses, it means that the hair cycle enters the anagen from the telogen. In the negative control group (CON), hair did not grow after 2 weeks, but in the DC group, hair began to grow from the 2nd week after application, and after 4 weeks, it was observed that hair was grown evenly and heartily in the larger number of individuals compared to the negative control group (FIG. 1).

(2) Change in Hair Length

Figure 2:
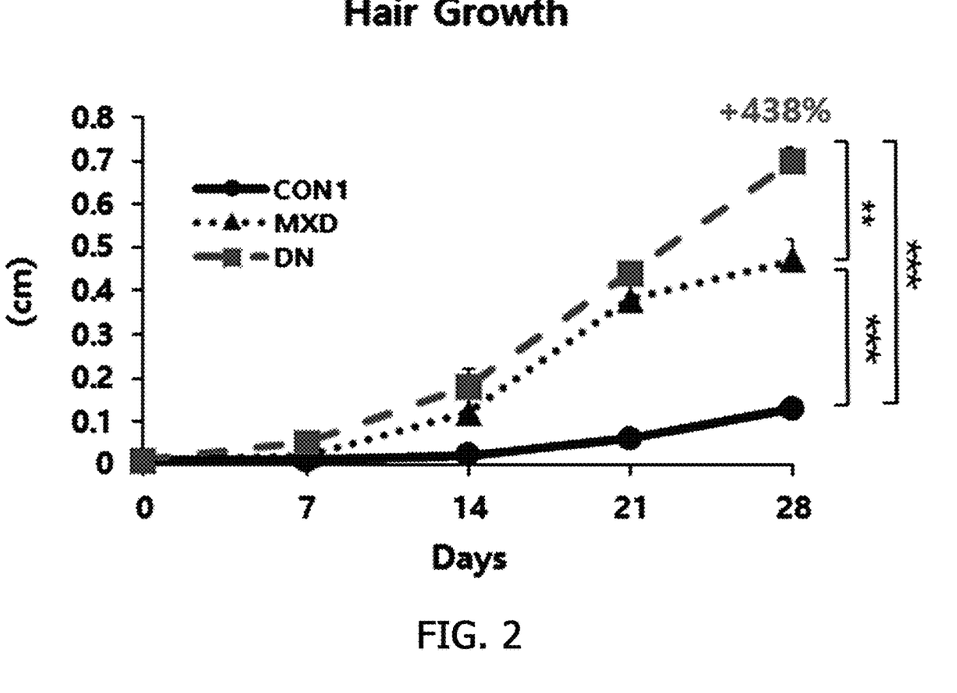
FIG. 2 is a graph illustrating hair length grown during a period of applying each sample in mice model which the hair is epilated. Each value is average±standard error of 5 mice. ns=p>0.05, **=p<0.01[one-way ANOVA, Tukey's experiment].

The hair length was measured weekly during the experimental period (4 weeks). The hair length of the DC group was significantly increased from the 2nd week compared to the negative control group, and significantly increased by 438% after 4 weeks (p<0.001) (FIG. 2). Therefore, it may be confirmed that Decanal is excellent for promoting the hair growth.

1-4. Histological Analysis of Back Skin

After 4 weeks of application, the animals were sacrificed and the back skin tissue sample was extracted with scissors and forceps around the area where the experimental material was applied, and fixed with formalin. After each step was dehydrated with alcohol and xylene, the back skin tissue sample was embedded with paraffin, and was cut into 5 μm slice using a microtome, and then paraffin was removed with alcohol and xylene. The slice was stained with Hematoxylin-Eosin, and histologic changes were observed with an optical microscope. A pathology speculum specialist was examined to evaluate the hair growth cycle, and quantity of hair follicle and diameter were measured on an optical microscope.

Figure 3A:
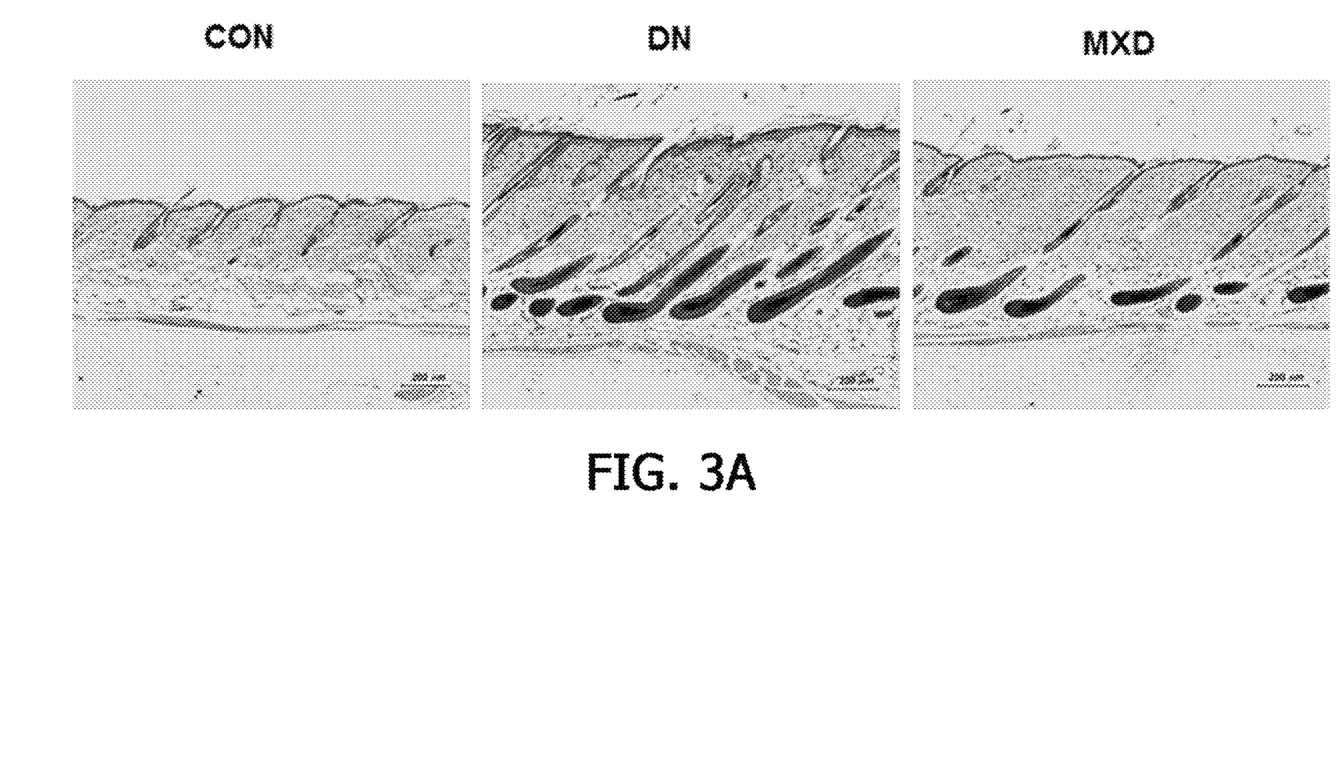
FIG. 3A illustrates a photograph illustrating the skin expression phenomenon of the hair follicle.
Figure 3B:
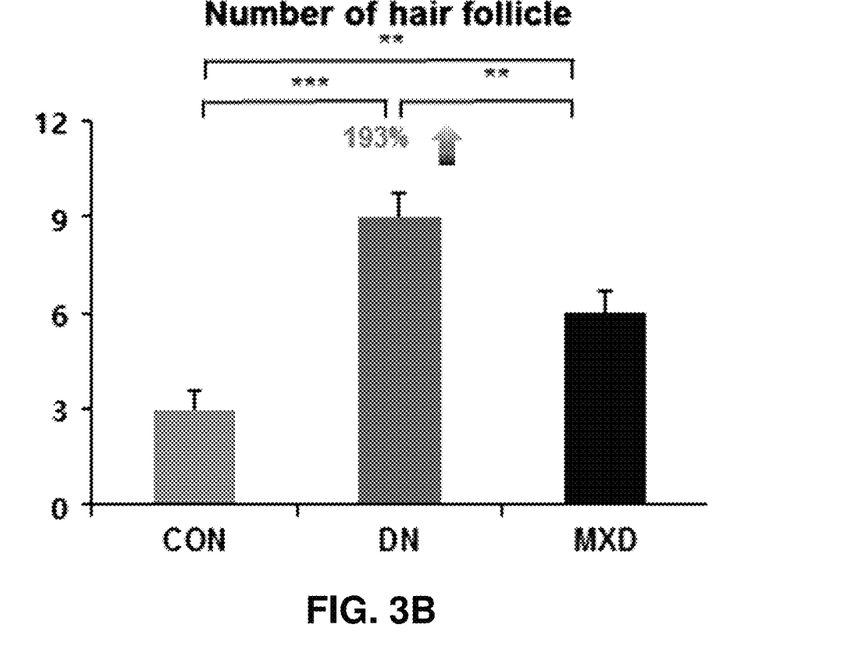
FIG. 3B illustrates a result of confirming an increase in the number of hair follicles.
Figure 3C:
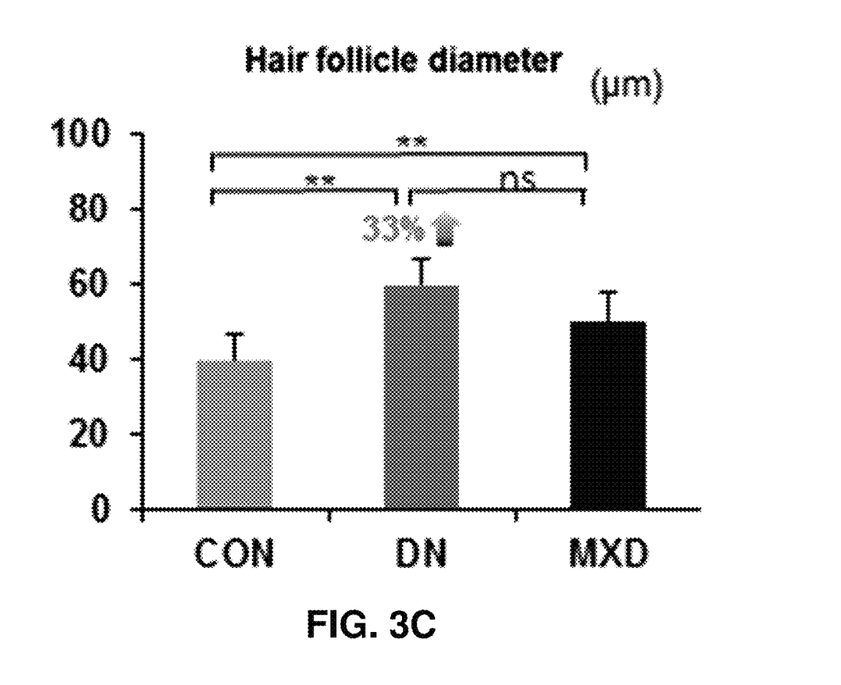
FIG. 3C illustrates the result of measuring the diameter of the hair follicle. Each value is average±standard error of 9 mice. ns=p>0.05, **=p<0.01 [one-way ANOVA, Tukey's experiment].

The results of measurement of the hair follicle number in each experimental group under an optical microscope of magnification of 40 are illustrated in FIG. 3.

In the DC group, both the number and size of hair follicles were increased, and a phenomenon that the hair follicle was lengthened and appeared outside the skin was observed (see FIG. 3A). It is considered that the phenomenon was related to the hair growth promoting effect of Decanal. In the DC group, the number of hair follicles was significantly increased by 193% compared to the negative control group (see FIG. 3B). In addition, As a result of evaluating a hair follicle diameter of each experimental group through image analysis, the hair follicle diameter was significantly increased by 33% in the DC group compared to the negative control group (see FIG. 3C).

Example 2. Regulation of Gene and Protein Expressions Related to Hair Growth of Mouse Skin Tissue by Decanal 2-1. Expression Analysis of Protein Related to Hair Growth Promotion in Skin Tissue (1) Western Blot Analysis Method A predetermined amount of visceral fat or liver tissue was homogenized with liquid nitrogen and lysis buffer in a mortar, and then centrifuged at 13,000×g at 4° C. for 20 minutes. And the middle layer was taken and the protein was quantified by the Bradford method. 50 μg of protein was electrophoresed on SDS polyacrylamide gel, electro blotted onto PVDF hyper film, and reacted with β-catenin and β-actin antibody (Cell Signaling Technology, Danvers, Mass., USA), respectively. Signals of each protein were visualized using a chemiluminescent detection system (Amersham) and the band thickness was quantified using Quantity One Analysis Software (Bo-Rad Laboratories).

(2) Analysis Result of Protein Expression Related to Hair Growth Promotion

Figure 4:
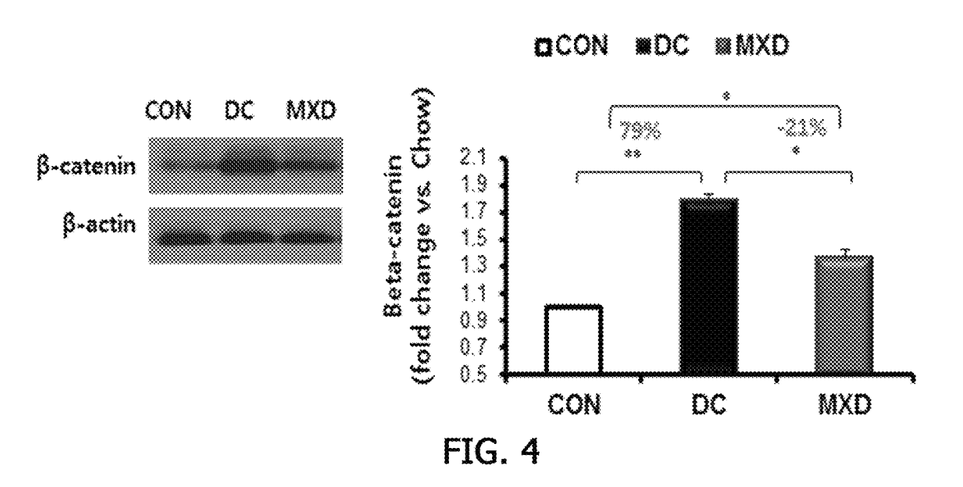
FIG. 4 illustrates change in protein expression of back skin tissues of the mice to which each sample was applied (western blot result on left and immunohistochemical results on right). The western blot result is average±standard error of 3 independent experiments in each group (n=2 or 3 for each experiment). ns=p>0.05, **=p<0.01[one-way ANOVA, Tukey's experiment].

The Wnt/β-catenin Signal transduction pathway is known to be involved in promoting entry into the anagen by regulating hair follicle cycle. The expression level of β-catenin was analyzed by western blotting in the back skin tissues in order to determine whether the signal transduction pathway related to hair growth promotion was activated. As a result, in the DC group, the protein expression in β-catenin was significantly increased by 79% compared to the negative control group, and this effect. And this effect was superior to the minoxidil group (FIG. 4).

2-2. Analysis of Gene Expression Related to Hair Growth Stimulation in Skin Tissue (1) RNA Isolation Method Using Trizol Method To quantitatively analyze total RNA in skin tissue of experimental animal, 1 mL of Trizol solution was added to 50-100 mg of skin tissue and homogenized, followed by centrifugation at 12,000×g for 10 minutes at 4° C. After transferring the supernatant liquid to a new tube, 200 μl of chloroform was added and the mixture was vigorously shaken. This process above was repeated twice, then the supernatant liquid was transferred to a new tube and isoprophanol and the supernatant liquid were added at a ratio of 1:1. The mixture was shaken 10 times and then allowed to stand at room temperature for 10 minutes, and the supernatant liquid was removed after centrifugation at 12,000×g for 10 minutes at 4° C., and 1 ml of 70% ethanol was added to the remaining precipitate, and the precipitate was centrifuged at 7,500×g and 4° C. for 5 minutes. After removing the ethanol, the tube containing the RNA precipitate was dried at room temperature for 5 minutes, and the RNA pellet was dissolved using nuclease free water. The concentration of RNA extracted at 260 nm and 280 nm wavelengths was measured using a UV/VIS spectrophotometer (Beckman coulter, DU730), and agarose gel electrophoresis was performed to confirm the integrity of the RNA sample.

(2) Reverse Transcription-Polymerase Chain Reaction (RT-PCR) Method cDNA was synthesized by performing reverse transcription using oligo dT primer and superscript reverse transcriptase (GIBCOBRL, Gaithersburg, Md., USA) after RNA isolation. The cDNA obtained by reverse transcription was determined as a template, and PCR was performed using the 5' and 3' flanking sequence of the gene cDNA to be amplified as primers. In this case, primers required were synthesized by a manufacture specialized company of primers (Bionia Co., Ltd., Korea), and the primer sequences were illustrated in Table 1 below. 2 μl of the reacted cDNA reaction mixture and 2.5 units of Taq polymerase (Takara, Japan) were added to a mixture prepared by adding 5 μl of 10× reaction buffer [100 mM KCL, 20 mM Tris-HCL (pH 8.0), 2.5 mM $MgCl_2$], 4 μl of 10 mM dNTP, and 1 μl each of 0.2 μM sense and antisense primer, and the volume was adjusted using 50 μl of distilled water, then PCR was performed using a PCR instrument. PCR conditions were set at 94° C. for 4 minutes, 94° C. for 30 seconds, 30 cycles [52° C. for 30 seconds, 72° C. for 45 seconds] and 72° C. for 10 minutes. Since 1 μl of the amplified product was electrophoresed on 1% agarose gel to check the DNA band, gene expression level was evaluated.

TABLE 1

| Gene | Primer | Base sequence (5'→3') | Annealing temperature (° C.) | PCR product (bp) |
|---|---|---|---|---|
| Wigless related MMTV integration site 10b (Wnt10b) | F | TTTTGGCCACTCCTCTTCCT | 61 | 183 |
| | R | TCCTTTTCCAACCGAAAACC | | |
| Frizzled receptor 1 (FZD1) | F | TTCTATGAACAGGCCTTTCGTTCT | 55 | 484 |
| | R | CCTCGTGTAGAACTTCCTCC | | |
| Low-density lipoprotein receptor-related protein 5 (LRP5) | F | AAGGGTCCACAAGGTCAAGG | 55 | 520 |
| | R | AGAAGCACAGATGGCTGCAC | | |
| Glycogen synthase kinase 3β (GSK3β) | F | TGTGTGAGGAACAGAACTCA | 48 | 244 |
| | R | CCTACAGCCCTAGTCATCAG | | |
| Axin | F | TGCAGAGTCCCAAAATGAATG | 55 | 108 |
| | R | GAGCCTGTCCTTGTGTAC | | |
| β-Catenin | F | ATGGCTACTCAAGCTGAC | 55 | 298 |
| | R | CAGCACTTTCAGCACTCTGC | | |
| Insulin-like growth factor (IGF1) | F | TCAACAAGCCCACAGGGTAT | 60 | 280 |
| | R | ACTCGTGCAGAGCAAAGGAT | | |
| Hepatocyte growth factor (HGF) | F | CGAGGCCATGGTGCTATACT | 54 | 290 |
| | R | ACACCAGGGTGATTGAGACC | | |
| Vascular endothelial growth factor (VEGF) | F | TCTTCAAGCCATCCTGTGTG | 60 | 165 |
| | R | GCGAGTCTGTGTTTTTGCAG | | |
| Keratocyte growth factor (KGF) | F | GACATGGATCCTGCCAACTT | 54 | 686 |
| | R | AATTCCAACTGCCACTGTCC | | |
| Glyceraldehyde-3-phosphate-dehydrogenase (GAPDH) | F | AGAACATCATCCCTGCATCC | 60 | 321 |
| | R | TCCACCACCCTGTTGCTGTA | | |

Figure 5A:
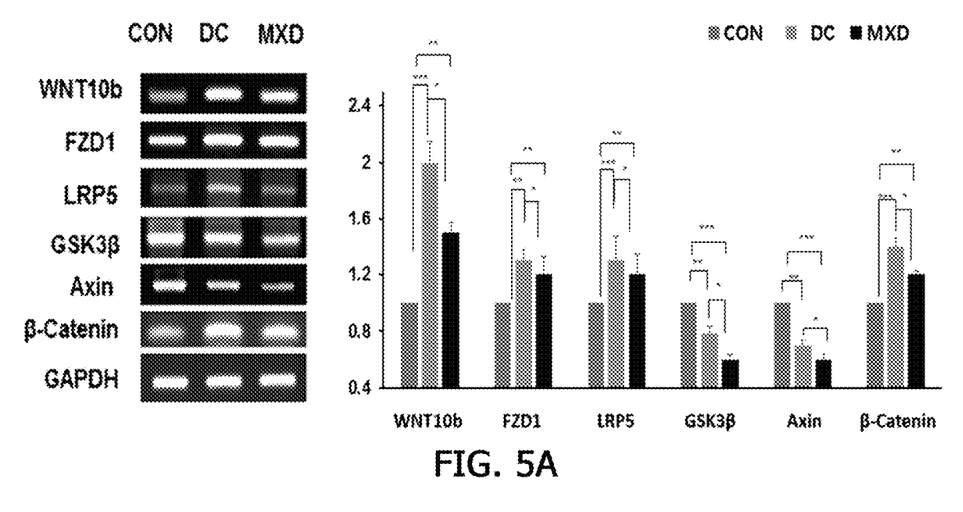
FIGS. 5A and 5B illustrates change in gene expression in back skin tissues of the mice to which each sample was applied. The western blot result is the average±standard error of 3 experiments in each group (n=2 or 3 for each experiment). ns=p>0.05, *=p<0.05, =p<0.01, *=p<0.001[one-way ANOVA, Tukey's experiment].

(3) Analysis Result of Gene Expression Regulation Related to Hair Growth Promotion The expression change of Wnt/β-catenin signal transduction material which was known as hair growth promotion mechanism in the back skin tissue of the mice to which the experimental material was applied for 4 weeks, was analyzed by RT-PCR. As a result, expressions of Wnt10b, FZD1 (frizzled receptor 1) which is a receptor of Wnt10b, and LRP5 (low-density lipoprotein receptor-related protein 5) were significantly increased in the DC group compared to the negative control group. Thus, gene expression of GSK3β (glycogen synthase kinase 3β) and Axin which expression were inhibited by Wnt10b, were significantly decreased in the DC group compared to the negative control group. Therefore, the expression of β-catenin was significantly increased in the DC group as compared to the negative control as the Wnt/β-catenin signal transduction pathway was activated (see FIG. 5A).

Figure 5B:
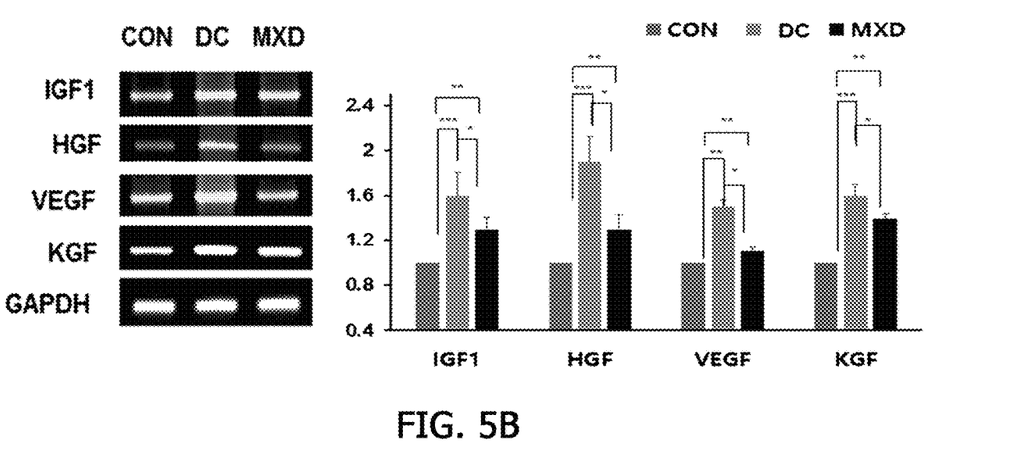

In addition, to investigate hair growth promoting action mechanism of Decanal, the expression change of endocrine factors affecting hair growth was evaluated. The gene expression level of insulin-like growth factor 1 (IGF1), vascular endothelial growth factor (VEGF), hepatocyte growth factor (HGF), and keratinocyte growth factor (KGF), which were growth factors affecting hair growth promotion in back skin tissue, was evaluated. As a result, all of the three genes significantly increased expression in the DC group as compared to the negative control (see FIG. 5B). Therefore, it can be confirmed that Decanal promotes regrowth of hair by increasing the expression of IGF1, HGF, VEGF and KGF in skin tissue, in addition to the mechanism of activating the hair follicle into the anagen by accelerating the growth of hair follicle length.

What is claimed is:

1. A method for promoting hair growth in a subject undergoing hair loss, the method comprising administering to the subject a composition including an effective amount of Decanal or a pharmaceutically acceptable salt thereof as an active ingredient to promote hair growth in the subject, wherein the active ingredient in the composition promotes hair growth in the subject,
   wherein the composition is topically applied to the subject's scalp, eyebrows, or eyelashes, and
   wherein the effective amount of Decanal or the pharmaceutically acceptable salt thereof is 0.001 mg/day to 1,000 mg/day.

2. The method of claim 1, wherein the composition is a formulation selected from a group consisting of a cream, a gel, a patch, a spray, an ointment, a plaster, a lotion, a liniment, and a paste as a skin external preparation.

3. The method of claim 1, wherein the composition is formulated as a tonic, a lotion, a cream, a spray, a mousse, a gel, a conditioner, a shampoo, or a rinse.

4. The method of claim 1, wherein the subject is a human.

5. The method of claim 1, wherein the composition comprises 0.0001 wt. % to 10 wt. % based on the total weight of the composition of Decanal.

6. The method of claim 1, wherein the composition comprises 0.01 wt. % to 100 wt. % based on the total weight of the composition of Decanal.

* * * * *